United States Patent
Haider et al.

(10) Patent No.: US 8,238,999 B2
(45) Date of Patent: Aug. 7, 2012

(54) METHOD FOR DISPLAY OF AT LEAST ONE MEDICAL FINDING

(75) Inventors: Sultan Haider, Erlangen (DE); Peter Kreisler, Buckenhof (DE); Klaus Küper, Tübingen (DE); Horst Allgaier, legal representative, Tübingen (DE); Matthias Philipp Lichy, Tübingen (DE); Heinz-Peter Schlemmer, Tübingen (DE)

(73) Assignee: Siemens Aktiengesellschaft, Munich (DE)

( * ) Notice: Subject to any disclaimer, the term of this patent is extended or adjusted under 35 U.S.C. 154(b) by 808 days.

(21) Appl. No.: 11/473,774

(22) Filed: Jun. 23, 2006

(65) Prior Publication Data
US 2007/0076931 A1    Apr. 5, 2007

(30) Foreign Application Priority Data
Jun. 23, 2005    (DE) .......................... 10 2005 029 244

(51) Int. Cl.
*A61B 5/05*    (2006.01)
(52) U.S. Cl. ........ 600/407; 600/425; 600/431; 328/128; 705/2
(58) Field of Classification Search .............. 600/407, 600/300, 431, 425; 328/128; 250/363.02; 705/2
See application file for complete search history.

(56) References Cited

U.S. PATENT DOCUMENTS

| | | | |
|---|---|---|---|
| 5,261,406 A * | 11/1993 | MacKay et al. | 600/431 |
| 5,740,801 A | 4/1998 | Branson | |
| 6,551,243 B2 * | 4/2003 | Bocionek et al. | 600/300 |
| 2002/0173721 A1 | 11/2002 | Grunwald et al. | |
| 2003/0146942 A1 * | 8/2003 | Helgason et al. | 345/968 |
| 2003/0194115 A1 | 10/2003 | Kaufhold et al. | |
| 2004/0078215 A1 * | 4/2004 | Dahlin et al. | 705/2 |
| 2005/0065424 A1 | 3/2005 | Shah et al. | |
| 2005/0107690 A1 * | 5/2005 | Soejima | 600/425 |
| 2006/0061595 A1 * | 3/2006 | Goede et al. | 345/619 |
| 2006/0101328 A1 * | 5/2006 | Albornoz et al. | 715/512 |
| 2006/0155577 A1 * | 7/2006 | Niemeyer | 705/2 |

FOREIGN PATENT DOCUMENTS

| | | |
|---|---|---|
| EP | 1 239 396 | 12/2001 |
| WO | WO 95/15521 | 6/1995 |
| WO | WO 2004/097709 | 11/2004 |

OTHER PUBLICATIONS

Eustace et al. "Whole body magnetic resonance imaging", British Medical Journal, BMJ Jun. 2004; vol. 328, pp. 1387-1388.*

* cited by examiner

*Primary Examiner* — Brian Casler
*Assistant Examiner* — Joseph M Santos
(74) *Attorney, Agent, or Firm* — Schiff Hardin LLP

(57) ABSTRACT

In a method for display of at least one medical finding, at least one part of a body of a patient is shown on a display medium in a body view. A localization in the body of the patient is associated with each finding, and the localizations are marked at a point in the body view corresponding to the localization. The display medium is interactively operable, and a data set associated with the corresponding finding is displayed on the display medium by interaction with a marked localization.

15 Claims, 2 Drawing Sheets

METHOD FOR DISPLAY OF AT LEAST ONE MEDICAL FINDING

BACKGROUND OF THE INVENTION

1. Field of the Invention

The present invention concerns a method for display of at least one medical finding.

2. Description of the Prior Art

In medical diagnostics, in particular imaging diagnostics, it is frequently necessary to process and to evaluate a large number of image data to create a finding. For example, it is possible to map the majority of the body of a patient by means of magnetic resonance tomography. For this purpose, generally several thousands of slices, from the head to the feet of the patient, are acquired by means of a magnetic resonance apparatus. Alternatively, within a partial body examination an overview can initially be created, followed by detailed examinations of specific regions (for example the brain, the upper body or the abdomen). For example, for cancer patients this technique allows a determination as to whether metastases have formed in the body. For this purpose, it is necessary for a doctor or radiologist to proceed through the data of the partial body examination slice-by-slice and, if applicable, to create a finding. To assess extensive examinations, it is often necessary to view findings originating from other examinations so as to take them into account in the finding. Under the circumstances, the doctor must review a large amount of data.

To make this easier for the doctor, it is known to list findings within a text protocol. This type of finding review is, however, is unwieldy for the treating doctor or radiologist since he or she does not have direct access to the associated image data from the text protocol. Such image data must be manually sought out from a databank in which they are archived. In particular, the individual images must be manually associated with various regions in the human body, for example head, upper body or back region. It may also be necessary to link measurement data from other examination methods (for example ultrasound or computed tomography) with the same body region, which increases the effort for the doctor.

A device that allows findings to be marked in a schematic representation of a human body is known from US 2004/0078215 A1. A user can have details of body regions displayed. Further findings can be added to the representation via the device. However, it is still necessary for the user to search manually for the image data belonging to the respective finding from the database by hand.

SUMMARY OF THE INVENTION

An object of the present invention to provide a method that clearly and comfortably allows the representation of findings of a patient.

This object is achieved by a method in accordance with the invention wherein at least one part of a body of a patient is shown on a display medium in a body view, with a localization in the body of the patient being associated with each finding and the localizations are marked at a point in the body view corresponding to the localization. The display medium is interactively operable, and a data set associated with the corresponding finding is displayed on the display medium through interaction with a marked localization. As used herein "body view," encompasses either a view of a part of the body of the patient or a view of the whole body of the patient. This body view, for example, can be a slice of a magnetic resonance examination in which a longitudinal section through the patient is mapped. The body view can be composed of a number of measurements that were implemented sequentially and joined into an overall image, namely body view.

By the markings of the findings on the body view, a doctor can easily receive an overview of where findings exist in the body of the patient. The graphical representation increases the clarity relative to a text-based listing of the findings. Added to this it is the capability for the doctor to easily obtain an overview of the propagation of the disease, for example in cancer patients. This makes an assessment of the health status of the patient easier. Additionally, a simple presentation is made to the doctor to allow display of a data set belonging to the respective finding in order to improve his or her overview. This represents a significant facilitation for the doctor, who no longer has to search in a database for the data sets belonging to the finding; rather, they can be directly displayed from the overview.

In an embodiment of the invention, a region of interest can be selected in the body view. In particular, this can be a region around a finding that the doctor would like to study in greater detail.

In another embodiment of the invention, an overview of all data sets available for the region of interest is automatically displayed. A simple possibility for surveying is thereby provided to the assessing doctor. Particularly when a number of existing medical assessments of the patient are available, the limitation of the view to the region of interest increases the clarity.

The survey is appropriately interactively operable. The doctor thus can cause a data set to be shown on the display medium in a simple manner. He or she can comfortably analyze the region of interest without having to individually search out the corresponding data sets. This would particularly be a significant effort given larger databases. Simple influences of diseases on the surrounding body region can be determined in an easy simple manner.

In a further embodiment of the invention, the data sets can have been acquired by means of various imaging modalities. All data sets of the various modalities and associated with the patient thus can be displayed collected in the overview. These various modalities can be magnetic resonance examinations, computer tomography examinations and ultrasound examinations. The mutual representation of the various data sets offers the doctor a simple possibility to provide an extensive overview of the health state of the patient.

In another embodiment of the invention, reference data corresponding to the region of interest are displayed from a databank. Such data can be image data of healthy tissue that can be drawn upon for comparison with the present image data of the patient. This makes the generation of a diagnosis easier for the treating doctor. Image data regarding typical clinical scenario (disease patterns) and that make a diagnosis of similar cases easier can be additionally present in the databank.

In a further embodiment of the invention, the magnitude of a pathology can be determined. The pathology may be a tumor, for example, size of which can be of decisive importance for diagnosis and therapy. The determination of the size can ensue, for example, by marking the tumor by the doctor with a computer mouse. Alternatively, the size can be determined automatically. For example, the course of a tumor treatment the size can be quantitatively detected and recorded in this manner in a simple manner.

DESCRIPTION OF THE PREFERRED EMBODIMENTS

In the following exemplary embodiment, findings are shown marked on a whole-body view of a cancer patient. The described method, however, is universally usable for all types of medical findings.

Figure 1:
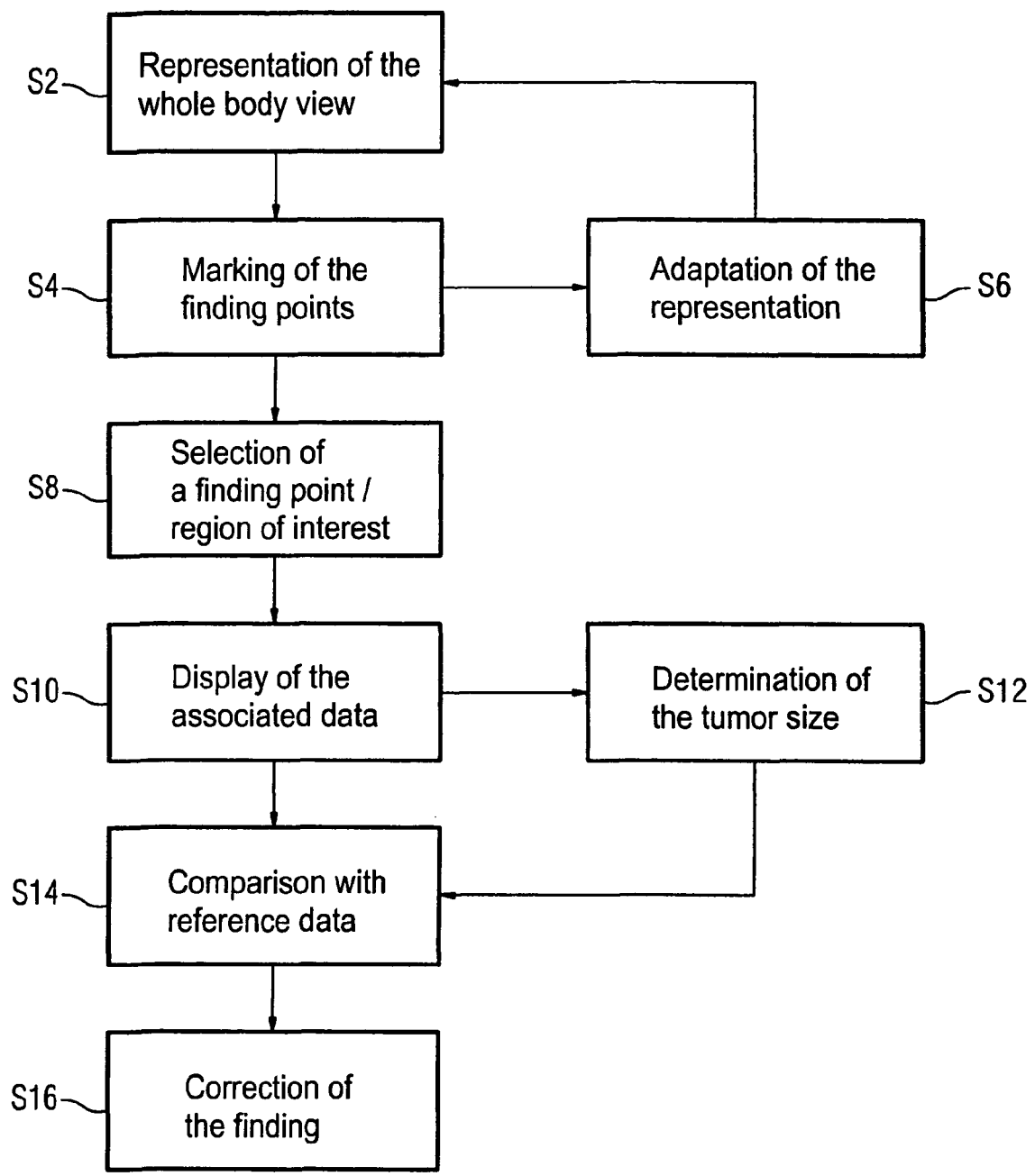
FIG. 1 is a schematic workflow diagram of a preferred embodiment of the invention and FIG. 2 is a schematic representation of a whole-body view with a finding overview on a display medium in accordance with the invention.

According to FIG. 1, a whole-body view of a whole-body examination (previously implemented by means of magnetic resonance tomography) is shown on a display medium in a first method step S2. In a second method step S4, the points in the body at which a tumor was determined are marked by a doctor. In a third step S6, the doctor now has the possibility to adapt the viewed representation according to his or her desires. For example, the doctor can modify the contrast, the marking of the finding points and the later display of associated finding data. The method hereupon continues with the first method step. S2 of the representation of the whole-body view. In a fourth method step S8, the doctor alternatively has the possibility to select a finding point or a region of interest by means of a computer mouse. A finding point is selected by clicking while the region of interest is selected by marking a region by dragging a marking frame with the computer mouse. The region of interest does not necessarily have to contain a finding. For example, it is possible that the doctor may discover a suspicious item on the whole-body view and may wish to analyze this more closely.

After the selection of the finding or of the region of interest, in a fifth method step S10 the data sets belonging to the finding or to the region of interest are shown on the display medium. For example, a cross-section image of the magnetic resonance examination associated with the finding or the region belongs to these data sets. If data sets of slices parallel to the cross-section image are likewise present, these can be additionally displayed. If further data sets from the region of interest exist, the doctor thus has the possibility to simply change the display or add to it with the computer mouse. The doctor thus can determine the influence of the tumor on the surrounding region in a simple manner making it easier to reach a diagnostic conclusion.

Furthermore, already-input findings in text form can be additionally displayed. Moreover, for example, data of a past measurement of the same region can be present that are likewise shown for comparison. For example, the course of a chemotherapy of the tumor can be assessed in a simple manner.

In an optional method step S12, it is possible to automatically determine the size of the shown tumor. For this purpose, the tumor size can be automatically evaluated by means of pattern recognition in the slices adjoining the shown slice. It can thus be determined in a simple manner whether the tumor has grown larger since the last examination. A comparison with reference data is enabled in a fifth method step S14. Such comparison data are, for example, data of a past examination of the same body region. Alternatively, for comparison it is possible to draw upon reference data from a databank that contains data about healthy tissue. In a sixth method step S16, the doctor has the possibility to correct or to expand the finding composed before the beginning of the method. The doctor can thereby in particular correct or expand text belonging to the finding. An updated text can be added, and representations of image data can be altered and optimized.

Figure 2:
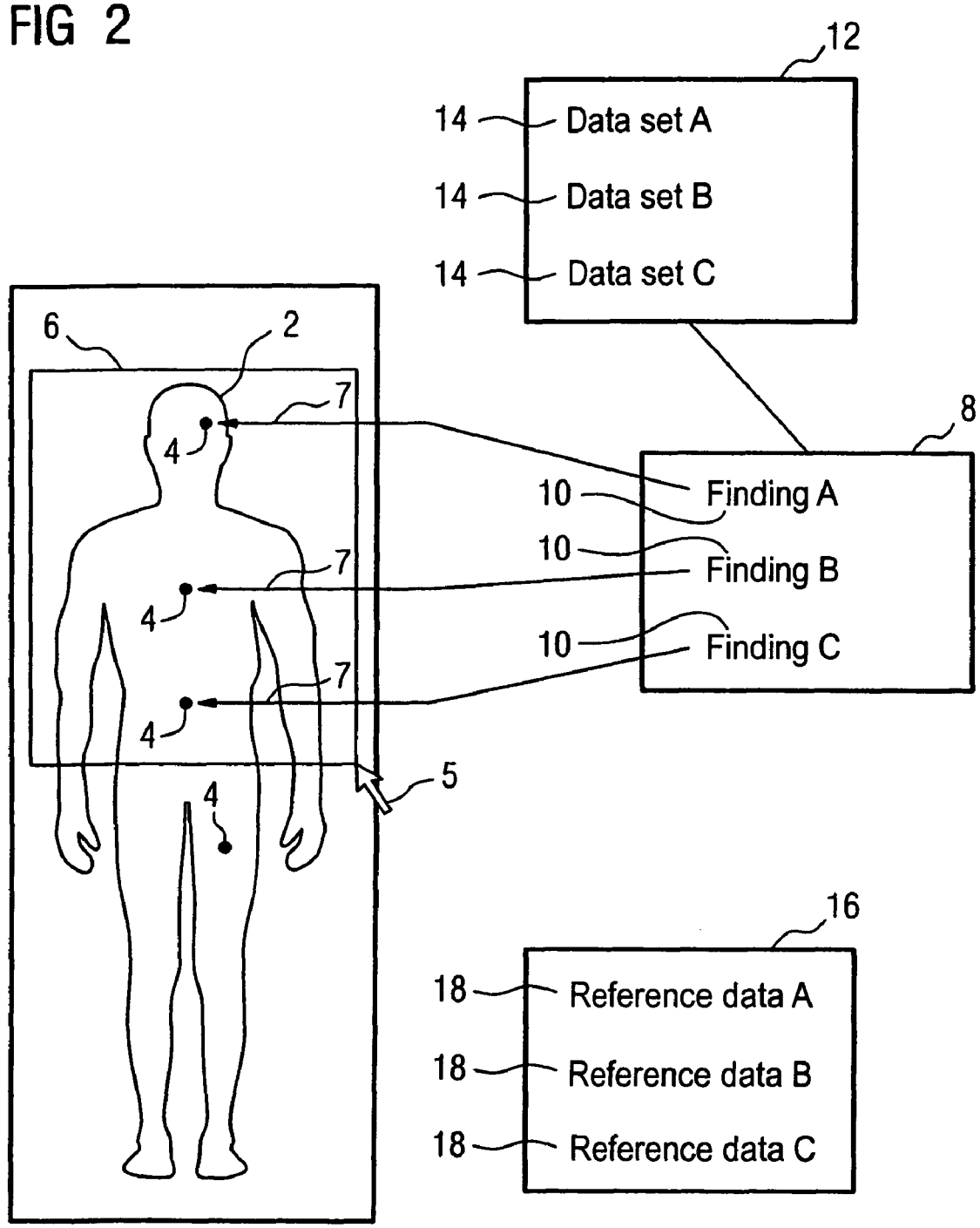

A whole-body view 2 of a patient is schematically represented in FIG. 2. One or more slices of a magnetic resonance examination belong to the whole-body view 2. It represents a longitudinal section through the patient. Existing finding points 4 are marked by points. By means of a pointer 5 that is operable with a computer mouse, a doctor has selected a region of interest 6 that comprises the upper body and head region. The finding points 4 within the region of interest are marked by arrows 7 that refer to a list 8 in which the findings 10 are listed.

The representation within the whole-body view has the great advantage that slices adjacent to the respectively represented slice can be made immediately accessible to the doctor. He or she can thus assess the dimensions of the tumor within adjacent slices in a simple manner. If a finding. 10 or a finding point 4 is selected within the computer mouse, a list 12 of the available data sets 14 regarding this finding is displayed. These can be both data sets 14 from various magnetic resonance examinations (for example with T1-weighting or T2-weighting) and data sets from other examination methods such as ultrasound or computer tomography. The associated image data are shown on the display medium by the selection of a data set 14, which here is not shown for better clarity. The available data sets 14 in particular include past examinations of the same patient. This is advantageous for the assessment of the course of a tumor treatment, for example by chemotherapy. In the examination of tumors, their size can be automatically determined by marking with the computer mouse. For this purpose, the data present in adjacent slices are automatically evaluated. The success of a tumor treatment can be simply quantified and assessed in this manner.

It is likewise possible to show on the screen reference data 18 of a healthy tissue from a databank 16, and thus to be able to produce a direct comparison between the finding and healthy tissue. Reference data 20 that show typical clinical scenarios of the region of interest for comparison with data sets 14 of the patient are likewise present in the databank 16.

The exemplary embodiment explained above refers to a tumor examination, but the invention and its embodiments are not limited to the display of tumor examinations. Rather, all possible finding points can be marked for overview in the whole-body view. It is not important whether the respective finding exists in text or image form. All examinations of a patient thus can be shown in the overview with the corresponding finding in a simple manner and be made comfortably accessible.

Although modifications and changes may be suggested by those skilled in the art, it is the intention of the inventors to embody within the patent warranted hereon all changes and modifications as reasonably and properly come within the scope of their contribution to the art.

We claim:

1. A method for displaying at least one medical finding to survey said at least one medical finding at a time subsequent to making said at least one medical finding, comprising the steps of:

obtaining image data from a patient currently undergoing an examination, and from said image data, generating an anatomical image showing at least one body part of the patient currently undergoing the examination;

displaying said anatomical image obtained from and showing at least one body part of the patient currently undergoing the examination on a display medium in a body view of the patient currently undergoing the examination;

generating a slice image that is not said anatomical image, of a section through said at least one body part from which a medical finding is discernible for the patient that currently undergoing the examination that is associated with a location in the body of the patient currently undergoing the examination, and manually electronically interacting with the body view of the patient currently undergoing the examination at said display medium to electronically mark, based on said slice image, any, freely selectable point in said body view that localizes the medical finding in said body view of the patient currently undergoing the examination;

in a database, storing at least one data set representing said slice image associated with the medical finding and, in said database, linking said data set with an identification of said point marked in said body view of the patient currently undergoing the examination that localizes the medical finding in said body view of the patient currently undergoing the examination; and at a point in time after storage of said medical finding in said database, selectively retrieving said medical finding from said data base by displaying said body view with said anatomical image therein on a survey medium and designating a location in said body view of the patient currently undergoing the examination on said survey display medium corresponding to the location in said body view of the patient currently undergoing the examination of the medical finding to be retrieved, and by matching the marked location in said body view of the patient currently undergoing the examination on said survey display medium with the localization of said medical finding linked to the medical finding in the database, automatically retrieving the slice image in which the medical finding is discernible from the database and displaying the slice image at said survey display medium.

2. A method as claimed in claim 1 comprising displaying only said portion of the body of the patient at said display medium as said body view.

3. A method as claimed in claim 1 comprising displaying a whole-body image of the patient at said display medium as said body view.

4. A method as claimed in claim 1 comprising designating said location in said body view of the patient on said survey display medium corresponding to the location in said body view of the patient of the medical finding to be retrieved by selecting a region of interest within said body view of the patient in said survey display medium by electronic interaction via said display medium.

5. A method as claimed in claim 4 comprising, at said survey display medium, automatically displaying a plurality of slice image data sets respectively for electronically marked points that exist within said region of interest.

6. A method as claimed in claim 5 comprising allowing manual interaction, via said display medium, with said slice image data sets within said region of interest to select at least one of said slice image data sets within said region of interest.

7. A method as claimed in claim 5 comprising displaying said information concerning said region of interest at said survey display medium adjacent to said region of interest.

8. A method as claimed in claim 5 comprising obtaining and storing said slice image data sets within said region of interest from previously-conducted medical examinations of said patient.

9. A method as claimed in claim 5 comprising storing, as said plurality of datasets, a plurality of slice image data sets respectively acquired with different medical imaging modalities.

10. A method as claimed in claim 5 comprising, at said survey display medium, additionally automatically displaying reference data from a data bank corresponding to said region of interest upon selection of said region of interest.

11. A method as claimed in claim 5 comprising storing, as said slice image data sets within said region of interest, slice image data sets obtained from the patient over time, that allow pathological changes in the patient over time to be identified.

12. A method as claimed in claim 5 comprising additionally selecting, with said slice image data sets within said region of interest, information concerning the region of interest comprising plurality of medical findings, and allowing modification of said medical findings by user interaction via said display medium.

13. A method as claimed in claim 5 comprising storing, as said plurality of slice image data sets, a plurality of magnetic resonance images.

14. A method as claimed in claim 5 comprising additional storing, with said plurality of slice image data sets, a plurality of text data sets comprise texts of respective findings.

15. A method as claimed in claim 14 comprising allowing additional text to be added to at least one of said texts by user interaction via said survey display medium.

* * * * *